United States Patent [19]

Eggers et al.

[11] Patent Number: 4,849,455

[45] Date of Patent: Jul. 18, 1989

[54] GLYCEROL CONTAINING VIRUCIDAL COMPOSITIONS

[75] Inventors: Hans J. Eggers, Cologne; Gerhard Schott, Mettmann, both of Fed. Rep. of Germany

[73] Assignee: Kruger GmbH & Co. KG, Fed. Rep. of Germany

[21] Appl. No.: 921,147

[22] Filed: Oct. 21, 1986

Related U.S. Application Data

[63] Continuation of Ser. No. 762,406, Sep. 5, 1985, abandoned.

[30] Foreign Application Priority Data

Aug. 21, 1984 [DE] Fed. Rep. of Germany ....... 3430709

[51] Int. Cl.$^4$ .............................................. A01N 31/00
[52] U.S. Cl. .................................... 514/724; 514/934
[58] Field of Search ................................. 514/724, 934

[56] References Cited

PUBLICATIONS

The Merck Index, 10th ed. (1983); pp. 265 and 644.
Remington's Pharmaceutical Sciences; 15th ed. (1975) p. 1088.
Chemical Abstracts; vol. 86 (1977), #101389a; Snipes et al.
Chemical Abstracts; vol. 55 (1961); #10573c; Popa et al.
Antiviral Research, Mar. 1983, pp. 25–41, Elsevier Biomedical Press, Antiviral Activity of an Alcoholic Hand Disinfectant. Comparison of the In Vitro Suspension Test with In Vivo Experiments on Hands, and on Individual Fingertips, Winfried Schurmann and Hans J. Eggers.

*Primary Examiner*—Leonard Schenkman
*Assistant Examiner*—Joseph A. Lipovsky
*Attorney, Agent, or Firm*—Wegner & Bretschneider

[57] ABSTRACT

A virucidal agent against naked vires containing at least 70% of methanol and/or ethanol and from 1 to 10% of glycerol and optionally, up of 5% of castor oil for improving the skin compatibility.

12 Claims, No Drawings

GLYCEROL CONTAINING VIRUCIDAL COMPOSITIONS

This application is a continuation of Ser. No. 762,406, now abandoned, filed Sept. 5, 1985.

The present invention relates to a virucidal agent against naked viruses which include, inter alia, polio virus 1, ECHO virus 11, ECHO virus 12, rota virus, reo virus 3 and adeno virus 2.

BACKGROUND OF THE INVENTION

It is known that viruses having a lipoid sheath are relatively sensitive and, thus, can be deactivated or even killed by the action of virucidal disinfectants known to date. A problem arises in combatting the naked viruses that are essentially more resistant to conventional disinfectants and, so far, could actually be killed only by applying formaldehyde at a relatively high concentration. However, formaldehyde is undesirable for toxicological reasons and is not applicable as a disinfectant for parts of the body either in laboratory tests or in clinical use.

The prior art literature on disinfecting or deactivating activities, respectively, of commercially available and skin-compatible disinfectants is contradictory. However, investigations conducted by the present inventors have resulted in the finding that most of the skin-compatible disinfectants are virtually ineffective against naked viruses. What has been reported on the effects of alcohols is also contradictory. Investigations conducted by the present inventors on the efficacy of isopropanol against naked vires showed that this alcohol is only very weakly active or ineffective against nakes viruses. These investigations further resulted in the finding that in a surprising manner ethanol and methanol are highly active and lose their activity only if they contain more than 30% of water. Thus, while ethanol acts as a disinfecting or deactivating agent, respectively, against bacteria and fungi even at a substantially lower concentration, the water content of the alcohols must be substantially reduced in order to accomplish a successful control or deactivation of nakes viruses.

As all alcohols, when applied to the skin, have an undesired effect of removing fat therefrom and rendering the skin brittle and chapped, it was a matter of choice to add skin-protecting agents to the alcohols such as to effect a restitution of the natural skin fat level. By corresponding investigations it has been found that, surprisingly, an addition of from 1 to 10% of glycerol to methanol and ethanol does not adversely affect the efficacy of these alcohols. It has further been found that additive amounts of up to 5% of castor oil also do not deteriorate the activity against naked viruses while the castor oil contributes to improve the skin compatibility.

SUMMARY OF THE INVENTION

The present invention relates to virucidal agents against naked viruses, which agents consist of at least 70% of methanol and/or ethanol and from 1 to 10% of glycerol. It is preferred that castor oil, in an amount of up to 5%, is further added to said virucides.

The present invention also relates to a method of disinfecting or deactivating naked vires by use of the aforementioned virucidal agents.

DETAILED DESCRIPTION OF THE INVENTION

Since the activity of the virucidal agents of the present invention rapidly decreases at an alcohol concentraton of less than 70%, the virucidal agents according to the present contain up to 97%, and preferably 80 to 90%, of methanol and/or ethanol. The amount of glycerol preferably is from 1 to 5%, and the additive amount of castor oil preferably is from 0.5 to 2%.

It is basically possible to include further skin-compatible materials in the agents of the present invention. However, an addition of triglycerides should be avoided, since these substances markedly reduce the virucidal agent activity. It is even possible that earlier findings indicating that the simple alcohols such as methanol and ethanol are not suitable for killing or deactivating naked viruses resulted from the fact of the skin fat being dissolved by the neat alcohols.

The addition of water to methanol and/or ethanol when intended as a virucidal agent of the present invention is not harmful as long as a sufficiently high concentration of methanol and/or ethanol is maintained.

The efficacy of the virucidal agent of the present invention has so far not been scientifically elucidated. The hypothesis that the activity is based alone on a dehydration effect cannot be correct, as other solvents having also a highly dehydrating effect such as propyl alcohol, isopropyl alcohol and acetone are inactive.

The choice of whether the virucidal agents of the present invention comprises methanol, ethanol or mixtures of the two alcohols depends on costs, toxicity and possible legal regulations of a commercial use of the two alcohols. Thus, while methanol is somewhat more efficient than ethanol, the former has a higher toxicity than the latter. On the other hand, ethanol is more expensive and in many countries is subject to special legal provisions that may impede or prohibit the use of ethanol for the preparation of the agents according to the invention. Since the activity of mixtures of methanol and ethanol increases with an increasing proportion of methanol in a linear relation, mixtures of the two alcohols may be readily employed as well so that a compromise may be found between the advantages and disadvantages of the two alcohols.

The virucidal agents of the present invention are so highly active that mostly within one minute (after a period of 15 minutes at the latest), the activity and infectiousness of the most frequent naked viruses are reduced by at least 4 powers of ten.

In practical application, the virucidal agents of the present invention may be used either as rinsing agents or applied to the skin by means of cotton, a cloth rag or a similar aid to the infected areas of the skin. With a view to the deactivating effect of triglycerides it is recommended that in a first application the skin fat is removed, and then in a second application the virucidal agent of the invention is allowed to display its action. The content of glycerol and, optionally, of castor oil, protects the skin from being rendered too dry and, thus, acts in a similar manner as would a per se desirable restitution of fat. Moreover, it is possible, after using the virucidal agents of the invention to treat the skin, to apply suitable skin cosmetics containing triglycerides, since the disinfection or deactivation, respectively, has been effected in the absence of triglycerides.

The composition and efficacy of the virucides of the present invention is further illustrated by way of the following non-limiting examples and comparative examples.

EXAMPLE 1

There are admixed 95 parts by volume of ethanol (96% by volume) with 4 parts by volume of castor oil and 1 part by volume of glycerol. In a second batch, the same amount of ethanol is admixed with 1 part by volume of castor oil and 4 parts by volume of glycerol. In accordance with further recipes, 97 parts by volume of methanol are admixed with 1 part by volume of glycerol and 2 parts by volume of castor oil or with 3 parts by volume of glycerol and 1 part by volume of castor oil.

Investigations with polio virus 1 (Mahoney) in the suspension test show that after 1 to 5 minutes, the infectiousness is decreased by from 3 to 5 powers of ten.

Comparative tests using corresponding solutions based on acetone, isopropanol and propanol did not show any detectable effect.

After increasing amounts of water had been added to the compositions, it was determined that compositions containing at least 70% by volume of methanol and/or ethanol are still strongly active. Compositions containing only 50% by volume of methanol or ethanol are ineffective.

Comparative tests using methanol and ethanol with the addition of 1 to 2% by volume of triglycerides (Eucerin) showed that these compositions were only very weakly active.

EXAMPLE 2

Skin regions were rubbed with neat methanol, neat ethanol, aqueous methanol, and aqueous ethanol, respectively, for comparative purposes. Thereby, these skin areas in the known manner were completely degreased and became dry. Comparative tests using the same alcohols containing added amounts of glycerol and/or castor oil showed that, although the skin was also degreased upon treatment, the skin retained its moisture.

What is claimed is:

1. A virucidal agent against viruses lacking lipid sheaths, comprising at least 70% by volume of methanol, ethanol, or mixtures thereof and from 1 to 10% by volume of glycerol.

2. The virucidal agent of claim 1, further comprising up to 5% of castor oil.

3. The virucidal agent of claim 2, wherein said castor oil is present in an amount of 0.5 to 2% by volume.

4. The virucidal agent of claim 1, wherein said methanol, ethanol, or mixtures thereof is present in an amount of up to 97% by volume.

5. The virucidal agent of claim 4, wherein said methanol, ethanol, or mixtures thereof is present in an amount of 80 to 90% by volume.

6. The virucidal agent of claim 1, wherein said glycerol is present in an amount of 1 to 5% by volume.

7. A method for disinfecting and/or deactivating viruses lacking lipoid sheaths comprising applying to the skin of a patient a virucidal agent comprising at least 70% by volume of methanol, ethanol, or mixtures thereof and from 1 to 10% by volume of glycerol.

8. The method of claim 7, wherein said virucidal agent further comprises up to 5% of castor oil.

9. The method of claim 8, wherein said castor oil is present in an amount of 0.5 to 2% by volume.

10. The method of claim 7, wherein said methanol, ethanol, or mixtures thereof is present in an amount of up to 97% by volume.

11. The method of claim 10, wherein said methanol, ethanol, or mixtures thereof is present in an amount of 80 to 90% by volume.

12. The method of claim 7, wherein said glycerol is present in an amount of 3 to 5% by volume.

* * * * *